US011540886B2

(12) United States Patent
Richter et al.

(10) Patent No.: US 11,540,886 B2
(45) Date of Patent: Jan. 3, 2023

(54) SURGICAL NAVIGATION SYSTEM PROVIDING ATTACHMENT METRICS

(71) Applicant: Medos International Sarl, Le Locie (CH)

(72) Inventors: Jörn Richter, Oberdorf (CH); Roger Berger, Oberdorf (CH)

(73) Assignee: Medos International Sarl

( * ) Notice: Subject to any disclaimer, the term of this patent is extended or adjusted under 35 U.S.C. 154(b) by 0 days.

(21) Appl. No.: 16/704,848

(22) Filed: Dec. 5, 2019

(65) Prior Publication Data

US 2020/0179061 A1 Jun. 11, 2020

Related U.S. Application Data

(60) Provisional application No. 62/775,444, filed on Dec. 5, 2018.

(51) Int. Cl.
| | | |
|---|---|---|
| G06T 19/00 | (2011.01) | |
| G06T 11/00 | (2006.01) | |
| A61B 34/20 | (2016.01) | |
| A61B 34/00 | (2016.01) | |
| A61B 34/10 | (2016.01) | |
| A61B 17/70 | (2006.01) | |

(52) U.S. Cl.
CPC .......... *A61B 34/20* (2016.02); *A61B 17/7059* (2013.01); *A61B 34/10* (2016.02); *A61B 34/25* (2016.02); *G06T 11/008* (2013.01); *G06T 19/003* (2013.01); *A61B 2034/104* (2016.02); *A61B 2034/105* (2016.02); *A61B 2034/107* (2016.02); *A61B 2034/2051* (2016.02); *A61B 2034/2055* (2016.02); *A61B 2034/2063* (2016.02); *A61B 2034/2065* (2016.02); *A61B 2034/2068* (2016.02); *G06T 2210/41* (2013.01)

(58) Field of Classification Search
None
See application file for complete search history.

(56) References Cited

U.S. PATENT DOCUMENTS

| | | |
|---|---|---|
| 6,533,737 B1 | 3/2003 | Brosseau et al. |
| 9,060,813 B1 | 6/2015 | Uribe |
| | (Continued) | |

FOREIGN PATENT DOCUMENTS

EP 3566669 A1 11/2019

OTHER PUBLICATIONS

International Search Report and Written Opinion (PCT/EP2019/083707); dated Feb. 20, 2020; 17 pages.
(Continued)

*Primary Examiner* — Tize Ma
(74) *Attorney, Agent, or Firm* — Dunlap Codding, P.C.

(57) ABSTRACT

A system and method for providing enhanced information to a surgeon is described. A three-dimensional reconstruction of a patient's anatomical structure selected for surgery and a representation of a surgical treatment apparatus are rendered on a display device. At least one attachment metric for a proposed attachment between the surgical treatment apparatus and the patient's anatomical structure is calculated using the three-dimensional position of the surgical treatment apparatus relative to the patient's anatomical structure. And, an indication of the attachment metric is rendered on the display device.

10 Claims, 7 Drawing Sheets

(56) References Cited

U.S. PATENT DOCUMENTS

| | | |
|---|---|---|
| 9,433,443 B2 | 9/2016 | Montello et al. |
| 9,861,446 B2 * | 1/2018 | Lang ................. A61F 2/3859 |
| 2006/0015030 A1 | 1/2006 | Poulin et al. |
| 2013/0060146 A1 * | 3/2013 | Yang ................. A61B 6/032 |
| | | 600/476 |
| 2014/0276001 A1 | 9/2014 | Ungi et al. |
| 2016/0191887 A1 * | 6/2016 | Casas ................ H04N 13/156 |
| | | 348/47 |
| 2017/0000562 A1 | 1/2017 | Frank et al. |
| 2019/0029757 A1 * | 1/2019 | Roh ................. G16H 50/00 |
| 2020/0035348 A1 * | 1/2020 | Sartor ............... G16H 30/40 |

OTHER PUBLICATIONS

International Preliminary Report of Patentability and Written Opinion (PCT/EP2019/083707); dated Jun. 17, 2021; 11 pages.

* cited by examiner

SURGICAL NAVIGATION SYSTEM PROVIDING ATTACHMENT METRICS

INCORPORATION BY REFERENCE OF RELATED APPLICATIONS

The present patent application claims priority to the provisional application U.S. Ser. No. 62/775,444, filed on Dec. 5, 2018; the entire contents of which are hereby expressly incorporated herein by reference.

FIELD OF THE DISCLOSURE

This disclosure relates generally to a surgical navigation system. More particularly, but not by way of limitation, this disclosure relates to a computer implemented system to assist in the placement of a surgical treatment apparatus through the use of an integrated database and software capable of calculating pertinent attachment metrics at a given position of the surgical treatment apparatus relative to a patient's anatomical structure.

BACKGROUND OF THE DISCLOSURE

The spinal column of bones is highly complex in that it includes over twenty bones coupled to one another to house and protect critical elements of the nervous system. In addition, the spine is a highly flexible structure, capable of a high degree of curvature and twist in multiple directions. The most flexible of all the regions of the spinal column is the cervical spine.

The bones and connective tissue of an adult human spinal column are coupled sequentially to one another by a tri-joint complex which consists of an anterior disc and the two posterior facet joints. The anterior discs of adjacent bones are separated and cushioned by cartilage spacers referred to as intervertebral discs. The vertebral bones of the spine are classified as cervical, thoracic, lumbar, and sacral. The cervical portion of the spine, which comprises the upper portion of the spine up to the base of the skull, includes the first seven vertebrae. The twelve intermediate bones comprise the thoracic vertebrae, and connect to the lower spine which comprises the five lumbar vertebrae. The base of the spine is the sacral bones (including the coccyx). The vertebrae which make up the cervical portion of the spine are generally smaller than those of the thoracic and lumbar spine.

Genetic or developmental irregularities, trauma, chronic stress, tumors, and disease are a few causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, and the individual variations in anatomy, determines the appropriate surgical protocol and implantation assembly. Using posterior plates for stabilization and immobilization of the cervical spine is known. A posterior plate is a narrow-elongated plate having a series of spaced holes through which fasteners, such as screws, may be inserted to fix the plate to the vertebrae. A pair of posterior plates is placed across the lateral posterior surfaces of a set of sequential cervical bones and is secured to the bone by using one screw per vertebra, thereby preventing the bones from moving relative to one another in either the vertical or horizontal planes.

Because the spine is routinely subject to high compression and torsional loads which cycle during movement, one of the primary concerns of physicians performing spinal implantation surgeries, and of the patients in whom the implants are placed, is the risk of fastener pulls-out. Fastener pull-out occurs when the cylindrical portion of the bone which surrounds the inserted fastener fails. A bone screw implanted perpendicular to the plate is particularly weak because the region of the bone which must fail for pull-out to occur is only as large as the outer diameter of the screw threads. It has been found that for some failure mods to occur for screws inserted into the bone at an angle regarding the plate, the amount of bone which must fail increases substantially as compared with screws implanted perpendicularly regarding the plate.

An additional concern with screws being implanted in the posterior side of the cervical spine is there are sensitive and important structures adjacent to the boney structures, such as the lateral masses and the laminae, which, because of their proximity to the implant, may be damaged by insertion or dislocation of screws. In the cervical spine, the vertebral arteries are disposed medially beneath the lateral masses or lamina and comprise critical structures which carrot be compromised. In addition, the facet joints which provide natural mobile coupling of sequential bones together must also be avoided if they are not indicated for fusion. Avoidance of these bodies has been a critical and ongoing concern regarding posterior screw insertion. Posterior plates of the prior art have provided little in the way of reasonable or practical solutions for ensuring proper screw insertion. Posterior screw plate assemblies necessarily include a plurality of screws inserted through a single plate. However, if a single screw loosens with respect to the surrounding bone into which it has been inserted, loss of fixation occurs and possible neurological repercussions may result.

One way to avoid the drawbacks of current plate systems has been to use fixation systems that employ polyaxial screws, rods, and hooks. A polyaxial screw can be inserted into the vertebral bone at a selected angle within a predetermined range of angles including non-perpendicular angles. This permits the surgeon to select the angle and direction for inserting the polyaxial screw into the bone to avoid sensitive areas, and increase the fixation between the polyaxial screw and the bone. However, while polyaxial screws provide a surgeon with the ability to locate the screws in optimum locations and directions, the ability to do so requires a high degree of skill and experience. Further, to ensure proper placement of polyaxial screws, surgeons typically utilize fluoroscopy for an extended period which can expose patients to unwanted radiation.

Surgeons, either operating by hand or the through use of robotic surgical equipment, often rely on surgical navigation systems when performing surgical procedures. Regarding spinal surgery, surgical navigation systems have been used with success in various procedures, but are particularly useful when the surgical field is obscured or the surgical procedure requires the three-dimensional visualization of the patient's anatomy, for example, during posterior cervical stabilization and fusion procedures. In these procedures, a bone plate is applied in a desired location on the spine, and then secured by driving screws, or polyaxial screws and rods, into the vertebrae.

An interactive computer-assisted surgical system is disclosed in U.S. Pat. No. 6,533,737. The computer-assisted surgical system comprises a computer including three-dimensional models of anatomical structures and a user interface including a position sensing system to register in real-time the relative positions of the anatomical structures of interest and of a surgical tool. Interactions between the surgical tool and the anatomical structure are measured, and then displayed on a monitor using the three-dimensional models. Multi-view display, transparency display and use of cutting planes allow the surgeon to visualize the interaction between the surgical tool and the anatomical structures any time during the surgical procedure. The surgical navigation system allows a surgeon to visualize patient anatomy and track the position of surgical tools. The surgeon may then utilize the surgical navigation system to use a surgical tool to mark locations on anatomical structures to determine a location to place a surgical implant at a desired position and orientation.

It is desirable to track the position of surgical treatment apparatuses with reference to patient anatomy for several reasons. For example, a posterior cervical stabilization and fusion procedure may consist of constructs utilizing polyaxial screws and plates. Crucial for the stability of these constructs is the screw-to-bone integration in the lateral mass. During the actual posterior cervical stabilization and fusion procedure, it is desirable for the surgeon to know the location and dimensions of the cervical vertebrae being treated to achieve strong screw-to-bone integration for stability. This information assists the surgeon in placing the surgical treatment apparatus. The surgical navigation system typically tracks the location of the surgical instrument in reference to the patient's anatomy and transmits the data to a processor to construct a coordinate system or a map indicating the real-time position of the surgical instrument. The surgeon may then refer to the coordinate system or map when placing the surgical treatment apparatus.

However, current surgical navigation systems and methods do not allow a surgeon to identify attachment metrics for a surgical treatment apparatus placement position. Whereas current surgical navigation systems may assist a surgeon in locating the general area that a surgical treatment apparatus should be placed, current systems do not aid a surgeon in identifying more precise placement locations that takes into account desirable attachment metrics. It is to such an improved surgical navigation system that the present disclosure is directed. The presently disclosed surgical navigation system may provide surgeons with data to more precisely identify surgical treatment apparatus placement locations and attachment metrics which may lead to improved patient outcomes.

BRIEF SUMMARY OF THE INVENTION

The present disclosure provides a surgical navigation system to support surgeons by determining and providing attachment metrics, such as placement of a surgical treatment apparatus, screw size selection, and screw trajectory. The surgical navigation system employs identifiers, a tracking system, and a computer system with an integrated database containing geometric data of the surgical treatment apparatus to determine and provide the surgeon with information indicative of one or more attachment metric, such as a screw placement, screw length, and screw trajectory for attaching the surgical treatment apparatus to a patient's anatomical structure.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale, or in schematic in the interest of clarity and conciseness. Not every component may be labeled in every drawing. Like reference numerals in the figures may represent and refer to the same or similar element or function. In the drawings.

DETAILED DESCRIPTION OF THE FIGURES

Before explaining at least one embodiment of the presently disclosed inventive concepts in detail, it is to be understood that the presently disclosed inventive concepts are not limited in their application to the details of construction, experiments, exemplary data, and/or the arrangement of the components as set forth in the following description or illustrated in the drawings. The presently disclosed inventive concepts are capable of other embodiments or of being practiced or carried out in various ways. Also, it is to be understood that the phraseology and terminology employed herein is for purpose of description and convenience and should not be regarded as limiting.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" or "one or more" will be understood to include one as well as any quantity more than one, including but not limited to, 1, 2, 3, 4, 5, 10, 15, 20, 30, 40, 50, 100, etc. The term "at least one" or "one or more" may extend up to 100 or 1000 or more depending on the term to which it is attached. In addition, the quantities of 100/1000 are not to be considered limiting, as lower or higher limits may also produce satisfactory results.

In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example.

Figure 1:
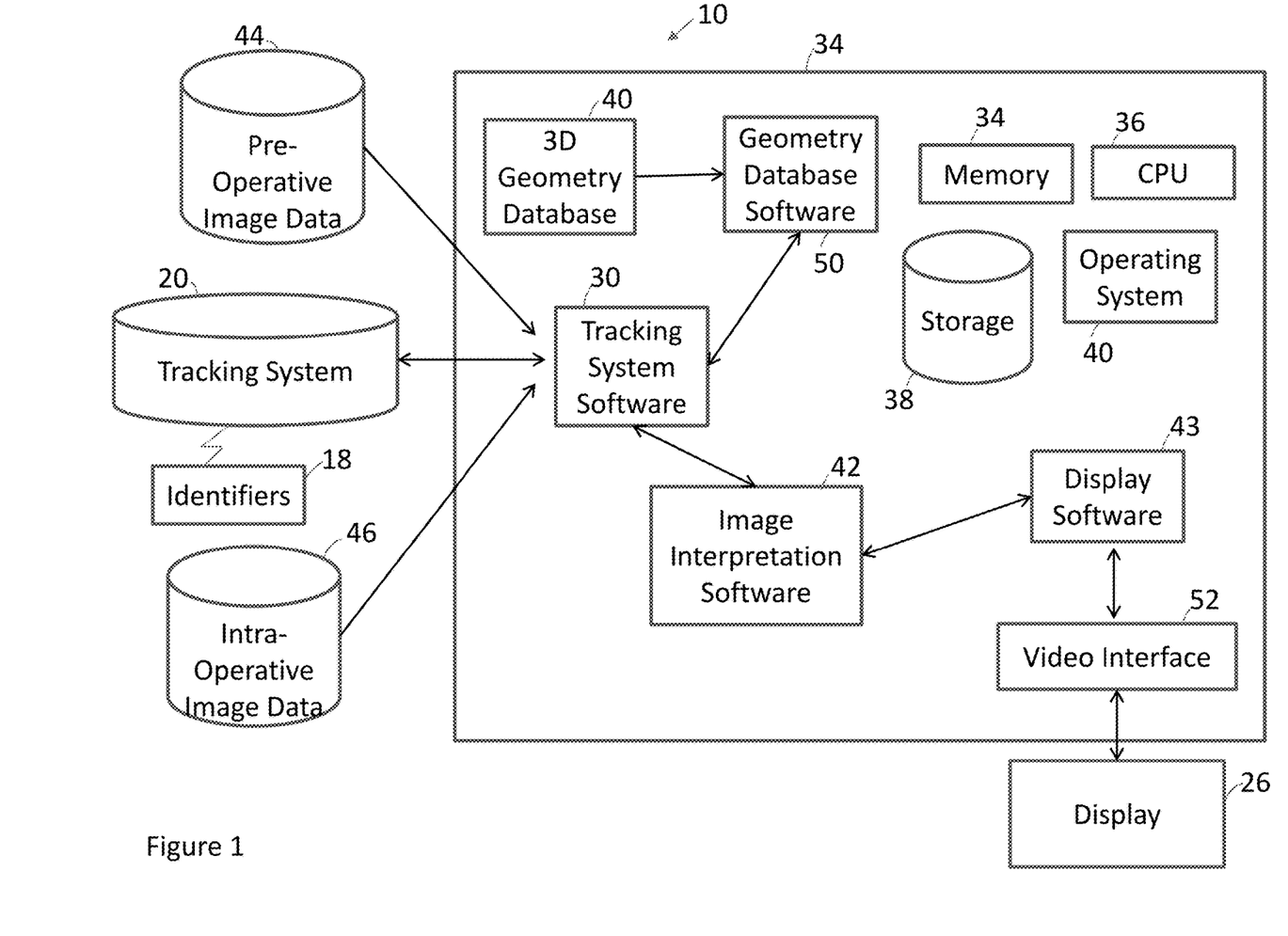
FIG. 1 is a schematic diagram of an embodiment of a surgical navigation system to aid in positioning and attaching a surgical treatment apparatus to a patient's anatomical structure, such as on lateral masses of a cervical spine.
Figure 2:
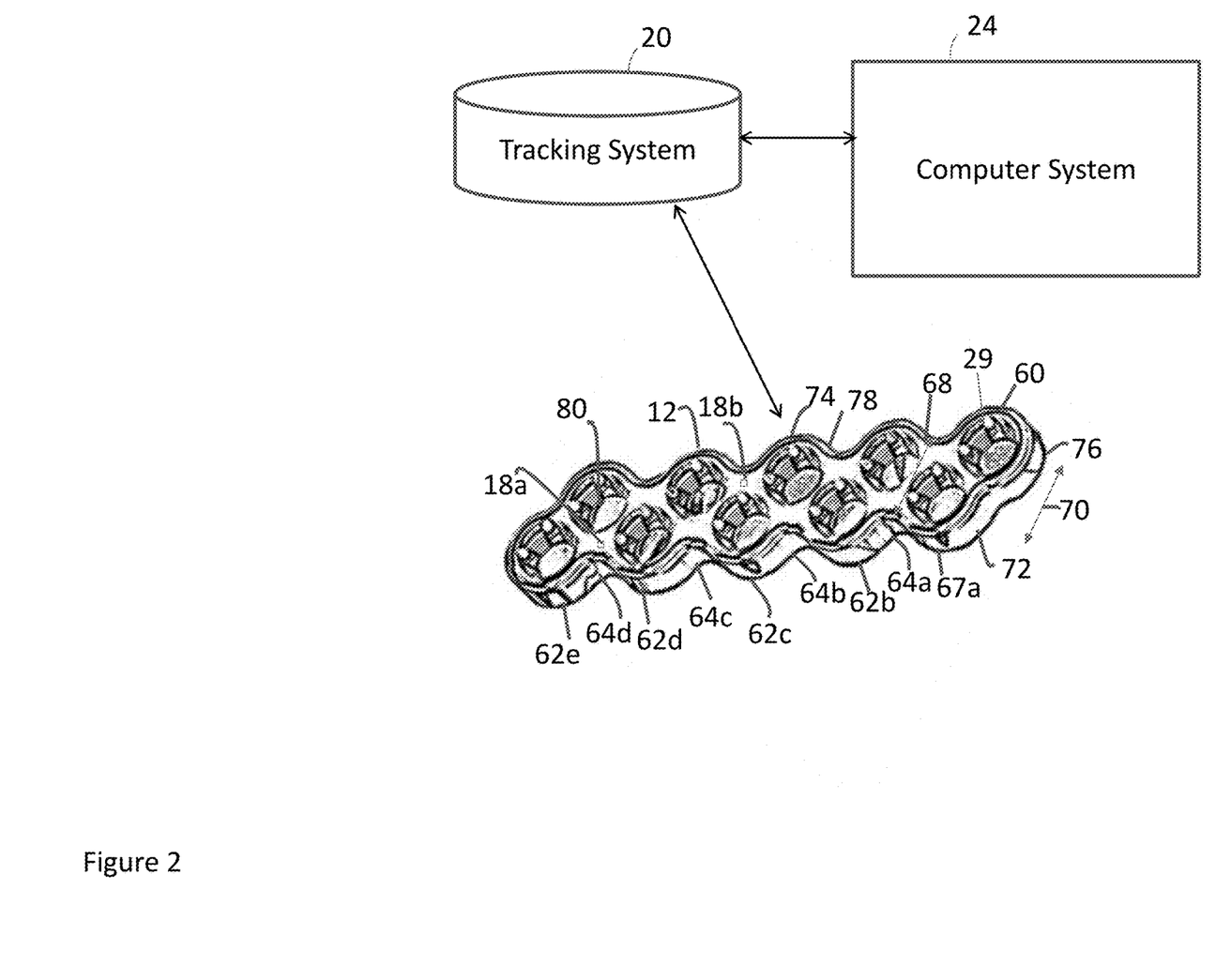
FIG. 2 is a schematic diagram of a tracking system constructed in accordance with the present disclosure that is configured to track a three-dimensional position and orientation of a surgical treatment apparatus in accordance with the present disclosure.

Referring now to the drawings and more particularly to FIGS. 1 and 2, shown therein is a surgical navigation system 10 in accordance with the present disclosure to aid in positioning of a surgical treatment apparatus 12 relative to a patient's anatomical structure 14 (see FIG. 5, for example), and corresponding fasteners (not shown) used to attach the surgical treatment apparatus 12 to the patient's anatomical structure 14. A variety of types of fasteners can be used in accordance with the present disclosure, such as screws, rivets, nails, clamps, or the like. The anatomical structure 14 can have one or more structures. For example, the anatomical structure 14 can be a spinal column having a plurality of structures known as vertebrae. The surgical treatment apparatus 12 may be a surgical implant, such as a bone plate. Examples of surgical implants include an anterior implant, a posterior implant and a lateral implant.

A suitable bone plate that can be used in accordance with the present disclosure is described in U.S. Pat. No. 9,433,443, the entire content of which is incorporated herein by reference. The surgical treatment apparatus 12 and the patient's anatomical structure 14 have one or more identifiers 18 attached thereto that are adapted to provide information to a tracking system 20 indicative of a location and orientation of the surgical treatment apparatus 12 relative to the patient's anatomical structure 14. Certain ones of the identifiers 18 can be attached to the surgical treatment apparatus 12, and the patient's anatomical structure 14. The surgical navigation system 10 also includes a computer system 24 in communication with the tracking system 20, and a display device 26 to display a computer augmented surgical field including a three-dimensional model of the patient's anatomical structure 14 overlaid with a graphical representation of the surgical treatment apparatus 12. The three-dimensional model of the patient's anatomical structure 14 is registered with an actual location and orientation of the patient's anatomical structure 14. Further, the graphical representation of the surgical treatment apparatus 12 is registered with an actual location and orientation of the surgical treatment apparatus 12. Thus, the display device 26 shows the user the location and orientation of the surgical treatment apparatus 12 and the location and orientation of the patient's anatomical structure 14.

The tracking system 20 monitors the location and orientation of the surgical treatment apparatus 12, and enables the computer system 24 to generate and display the real-time, three-dimensional representation of the location and orientation of the surgical treatment apparatus 12 on the display device 26. The tracking system 20 may utilize one or more tracking technologies that are well known and recognized by those skilled in the art, such as a video camera and suitable tracking system software 30 to determine the position and orientation of the identifiers 18. This information can be correlated with known information regarding the surgical treatment apparatus 12, and the patient's anatomical structure 14. The identifiers 18 may be reference assemblies or sensors that are embedded or attached to the surgical treatment apparatus 12 and the patient's anatomical structure 14. Identifiers 18 may be permanently attached or may be removable.

Further referring to FIG. 1, components and software of a computer system 24 used to perform various processes of the present disclosure is shown. The tracking system 20 is adapted to obtain geometric data indicative of a location and orientation of the identifiers 18, and transmit geometric data to the computer system 24. The computer system 24 may have at least one non-transitory computer readable medium (e.g., a memory unit 34), at least one CPU 36, at least one storage unit 38, and an operating system 40. An exemplary positioning system that can be used for the tracking system 20 is described in U.S. Pat. No. 6,533,737.

The computer system 24 has a plurality of software programs that work together to utilize raw data inputs from one or more sources to determine the attachment metrics for attaching the surgical treatment apparatus to the patient's anatomical structure. For example, FIG. 1 shows the computer system 24 running the tracking system software 30 configured to process raw geometric data from the tracking system 20, a 3D geometry database 40 capable of providing three-dimensional geometric data of the chosen surgical treatment apparatus 12, an image interpretation software 42 configured to calculate surgical treatment apparatus 12 placement metrics, and a display software 43 configured to display a real-time, three-dimensional reconstruction of the surgical field superimposed with the three-dimensional representation of the chosen surgical treatment apparatus 12. The computer system 24 is configured to access a pre-operative image data database 44, and an intra-operative image data database 46. The computer system acquires and utilize pre-operative image data in the pre-operative image data database 44, and intra-operative image data in the intra-operative image data database 46 obtained, for example, through MRI, CT, or X-ray imaging, that is indicative of a three-dimensional model of the patient's anatomical structure 14. The image data may be a tomography image or a three-dimensional ultrasound image.

The identifiers 18 attached to the surgical treatment apparatus 12 provide data regarding the position and orientation of the surgical treatment apparatus 12 to the computer system 24. The computer system 24 also executes geometry database software 50 that accesses the 3D geometry database 40 and provides information indicative of the three-dimensional shape of the surgical treatment apparatus 12 to the tracking system software 30. The 3D geometry database 40 contains the geometries of a single surgical treatment apparatus 12 or multiple different surgical treatment apparatuses 12. Image data (e.g., slice images of the patient's anatomical structure 14 forming a tomography of the anatomical structure 14) from one or more pre-operative scans is also provided to the computer system 24 from the pre-operative image data database 44.

The various data inputs are then utilized by their corresponding software modules. For example, tracking system data generated by the tracking system 20 will be processed by the tracking system software 30 and information within the 3D geometry database 40 will be processed by the geometry database software 50. The data from each of the various software modules are then utilized by the image interpretation software 42 to generate the attachment metrics.

The computer system 24 is also provided with a video interface 52 that receives commands from the display software 43, and converts the commands into video signals for display on the display device 26.

Shown in FIG. 2 is an exemplary embodiment of the surgical treatment apparatus 12. In this embodiment, the surgical treatment apparatus 12 is a bone plate 60 of a posterior vertebral plating system described by way of example in U.S. Pat. No. 9,433,443. Although intended for use primarily in the cervical portion of the spine, it should be understood that the posterior vertebral plating system may be used on any bony structure of the spine, including lumbar, thoracic, and sacral, and the posterior vertebral plating system can be used in any direction, e.g., posterior, anterior, or lateral.

The posterior vertebral plating system includes the bone plate 60 and a plurality of fasteners (not shown). In one embodiment, the fasteners can be variable angle locking screws that can be placed at a variety of trajectories relative to the bone plate 60. Variable angle locking screws are described, for example, in U.S. Pat. No. 9,433,443.

The bone plate 60 is intended to stabilize multiple adjacently disposed vertebrae. To this end, the bone plate 60 has a length dimensioned to extend along the posterior side of at least two vertebrae. It will be appreciated that the length of the bone plate 60 may be varied depending on the number of vertebrae to be stabilized. Because the bone plate 60 is intended to be fixed to bony structures of the posterior side of vertebrae (e.g., lateral mass, lamina), the plate 60 has a width and shape that allows the bone plate 60 to be positioned over the bony structures of the posterior side of adjacent vertebrae. In one embodiment, the bone plate 60 may have an overall width in a range from about 8 mm to about 14 mm, but more desirably, less than about 12 mm. The width of the bone plate 60 may be varied or curved or contoured along one side so the bone plate 60 is configured to have a plurality of nodes 62 (five of the nodes being labelled with the reference numerals 62a-62e for purposes of clarity) which define recesses 64 (four of the recesses being labelled with reference numerals 64a-64d for purposes of clarity) between each of the nodes 62 to reduce the outer contour and size of the bone plate 60. To this end, the bone plate 60 may have at least one minor width 68 at a most narrow portion and at least one major width 70 at a widest portion. In one embodiment, the minor width 68 may be approximately 5 mm and the major width 70 may be in a range of approximately 9 mm to 12 mm. The reduced width portion between each of the nodes 62 provides an area of reduced material for bending of the bone plate 60 as may be required by the spinal anatomy, as well as provides for better visualization of the bony surface below the bone plate 60. The bone plate 60 has a thickness 72, which may be in a range including, but not limited to, about 1 mm to about 4 mm, for example.

The bone plate 60 has an upper surface 74 and a lower surface 76. The bone plate 60 can include a rounded upper edge 78 to reduce irritation of surrounding tissue. The rounded upper edge 78 reduces the amount of trauma or irritation experienced by the surrounding soft tissue. The lower surface 76 of the bone plate 60 may be configured to conform to the contour of the vertebral bodies at each of the instrumented levels of the spine. In some embodiments, the lower surface 76 can be provided with a textured surface (not shown) which may include a variety of geometric shapes and/or protrusions, such as spikes, or other features, such as ridges, posts, pockets, or be treated such as bead blasted, porous coated, or acid etched to enhance its grip on the vertebral body. The bone plate 60 may also have a longitudinal and/or transverse curvature to match the corresponding attachment surface (e.g., the curve of the spine).

The bone plate 60 has a plurality of holes 80 which extend through the bone plate 60 from the upper surface 74 through the lower surface 76. The holes 80 are dimensioned and arranged relative to one another so that more than one of the holes 80 is positionable or alignable over the posterior bony structures, such as the lateral mass or lamina, of each vertebra to define a plurality of fixation points per vertebra. The holes 80 may be arranged in a variety of ways to provide multiple points of fixation while maintaining the structural strength and rigidity of the bone plate 60. The holes 80 are in such a way that at least two to three of the holes 56 is positionable over a single vertebra to define a plurality of fixation points per vertebra. In one version, the holes 80 may be arranged in at least two longitudinal rows of holes 80 along the length of the bone plate 60 with the holes 80 of one longitudinal row of holes being staggered and nested relative to the holes 80 of the other longitudinal row of holes 80.

One or more identifiers 18 are positioned on the upper surface 74 of the bone plate 60 to be visible to a camera of the tracking system 20. The identifiers 18 can be printed, embossed, or otherwise affixed to the upper surface 74, for example. The identifiers 18 can be spaced apart on the upper surface 74 a fixed and known distance apart so the exact three-dimensional location in space (relative to the camera) can be determined using triangulation techniques, for example. The identifiers 18 may also be printed, embossed, or otherwise affixed to a bone plate holder (not shown) which attaches to the bone plate 60 at a defined interface position. The tracking system 20 may include other types of position and orientation sensing systems, such as a magnetic position sensing system. In such a system, the camera is replaced by a magnetic field sensor and the identifiers 18 include magnetic field emitters.

The image interpretation software 42 receives information indicative of: the three-dimensional model of the bone plate 60 from the 3D geometry database 40, the three-dimensional model of the patient's anatomical structures 14, e.g., vertebrae of the spine via the pre-operative image data in the pre-operative image data database 44, and intra-operative image data from the intra-operative image data database 46. The image interpretation software 42 uses the information to identify and classify each hole 80 to determine one or more attachment metric such as an optimal fastener length, an optimal fastener direction, a critical structure avoidance angulation, and a fastener pull-out performance for use in attaching the bone plate 60 to the patient's vertebrae, for example. The optimal fastener length, and the optimal fastener direction, can be determined with the aid of a fastener-in-bone integration algorithm executed by the CPU 36 of the computer system 24. The fastener-in-bone integration algorithm can be implemented by analysing a current position of the bone plate 60 overlying the anatomical structures 14 to determine a maximum distance from an entry side of the anatomical structure 14 to an exit side of the anatomical structure 14. For each hole 80, the maximum distance from the entry side to the exit side is calculated for various fastener directions. The largest maximum distance is then used to determine the fastener direction. Once the fastener direction is determined, the fastener length can be determined by subtracting a predetermined amount from the maximum distance to avoid having the fastener exit the anatomical structure. 14. The fastener-in-bone integration algorithm may be input into the image interpretation software to classify each individual hole 80 based on a given set of variables. Variables can include degree of avoidance of critical anatomical structures, fastener pull-out performance, access direction and size, and the inclusion or exclusion of anatomical structural candidates for fastener placement. For example, the fastener-in-bone integration algorithm can provide predefined ideal fastener angulations relative to the sagittal plane to avoid penetration into predefined critical anatomical structures. Optimal fastener angulation can be determined by identifying the angulation that deviates least from the predefined ideal fastener angulation. Similarly, the fastener-in-bone integration algorithm can provide predefined fastener angulations that promote penetration of other anatomical structures identified by the surgeon for fastener placement. Fastener pull-out performance can be determined by calculating a wedge angle, for example, formed between the superior and inferior endplates of a fractured vertebra. Optimal pull-out performance can be determined by identifying the greatest wedge angle produced.

The computer system 24 obtains the data inputs from the tracking system 20, the 3D geometry database 40, and pre-operative image data database 44 to calculate various attachment metrics for securing the surgical treatment apparatus 12 to the patient's anatomical structure 14. Exemplary attachment metrics include hole placement, fastener length, and trajectory for each individual fastener used to attach the surgical treatment apparatus 12 to the patient's anatomical structure 14. The attachment metrics may be determined for each hole 80 in the bone plate 60 and displayed on the display device 26. In particular, the information with respect to the hole placement, fastener length, fastener trajectory for each individual hole 80, and classification data compiled by the image interpretation software 42 is then channelled through the video interface 52 to generate real-time images or video on the display device 26. Intra-operative image data including location and orientation of the bone plate 60 relative to the patient's anatomical structure 14 may be provided to the computer system 24 continuously or at given time intervals. This data is utilized by the tracking system software 30 to update the location and orientation data of the surgical treatment apparatus 12 throughout the surgical procedure. The input of new intra-operative image data into the intra-operative image data database 46 is operable to trigger the image interpretation software 42 to engage in the recalculation of the pertinent attachment metrics at the updated position.

A surgeon may determine surgical treatment apparatus 12 placement on the patient's anatomical structure 14 based on the number of holes 80 available that are capable of aligning with the patient's anatomical structure 14 to provide access for the surgical fastener to infiltrate the anatomical structure 14 and secure the surgical treatment apparatus 12 in place.

Figure 3:
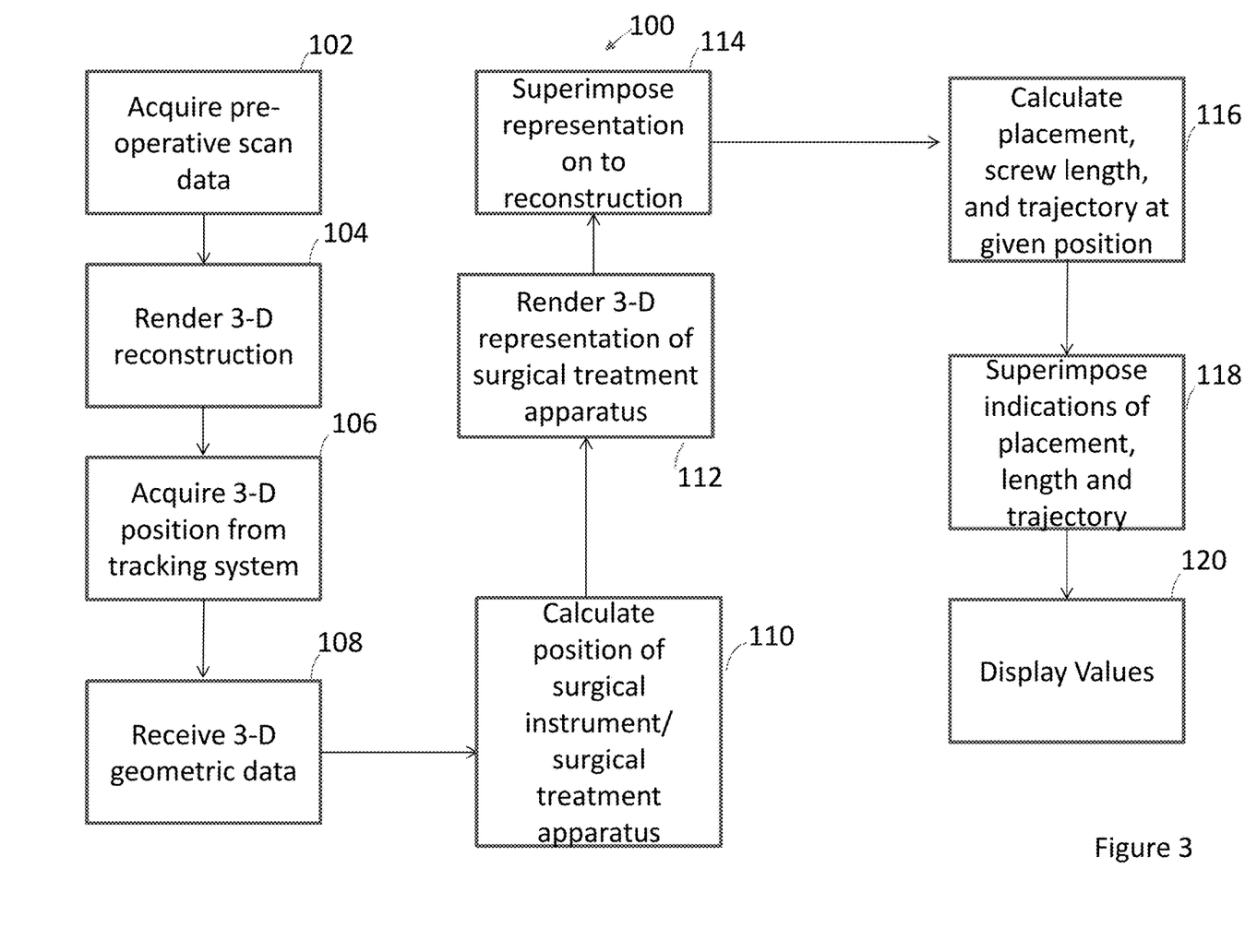
FIG. 3 is a flowchart of an exemplary embodiment of program logic according to the instant disclosure that superimposes a registered three-dimensional representation of the surgical treatment apparatus on a reconstruction of a patient's anatomical structures, and provides at least one attachment metric to the surgeon in accordance with the present disclosure.

Referring now to FIG. 3, a flow chart 100 describing the operation of the computer system 24 of this disclosure is shown. For example, in a surgical implant procedure, the computer system 24 is used to track the position of the surgical treatment apparatus 12 and to calculate the placement, length, and trajectory of each individual fastener used to attach the bone plate 60 to the patient's anatomical structure 14.

Initially, as represented by step 102, the computer system 24 acquires the pre-operative imaging data of the patient from the pre-operative image data database 44. As discussed above, the pre-operative imaging data can be a tomography image obtained using an X-ray, MRI, or CT scanning machine. The pre-operative image data can be analysed with the three-dimensional data of the bone plate 60 to calculate an estimated placement location for the bone plate 60 to maximize the attachment strength of the bone plate 60 to the anatomical structure 14. In step 104, the computer system 24 renders a three-dimensional reconstruction of the surgical field represented by the pre-operative imaging data. Once a three-dimensional reconstruction has been rendered, the computer system 24 acquires the three-dimensional position of the surgical treatment apparatus 12 in step 106 through the tracking system 20. Then, as represented by step 108, the computer system 24 receives the three-dimensional geometric data of the surgical treatment apparatus 12 being used in the procedure. The computer system 24 then calculates the position and orientation of the surgical treatment apparatus 12 based on the position of the surgical treatment apparatus 12 and the known geometric data of the surgical treatment apparatus 12 in step 110. As shown in step 112, the computer system 24 then renders a three-dimensional representation of the surgical treatment apparatus 12. In step 114, the computer system 24 superimposes the digital, three-dimensional representation of the surgical treatment apparatus 12 onto the corresponding position of the three-dimensional reconstruction of the patient's anatomical structure 14. As shown in step 116, the computer system 24 then calculates various attachment metrics such as the fastener-in-bone integration of the surgical treatment apparatus 12, and the corresponding length and trajectory of the fastener to achieve said fastener-in-bone integration for each hole 80 in the surgical treatment apparatus 12. The computer system 24 in step 118 then superimposes visual indications regarding attachment metrics such as fastener-in-bone integration, fastener length, and trajectory on the three-dimensional representation of the surgical treatment apparatus 12. For example, the computer system 24 can display a green circle registered on one of the holes 80 to indicate that the fastener-in-bone integration through this hole 80 is very strong when a fastener can infiltrate the bone a distance greater than 12 millimeters, for example. For another example, the computer system 24 can display a small dot to indicate the trajectory for a fastener to achieve an optimal fastener-in-bone integration. Finally, as represented in step 120, the computer system 24 can display the superimposed digital representation of the surgical treatment apparatus 12, three-dimensional reconstruction of the surgical site, and the various indications of the attachment metrics on the display device 26.

Figure 4:
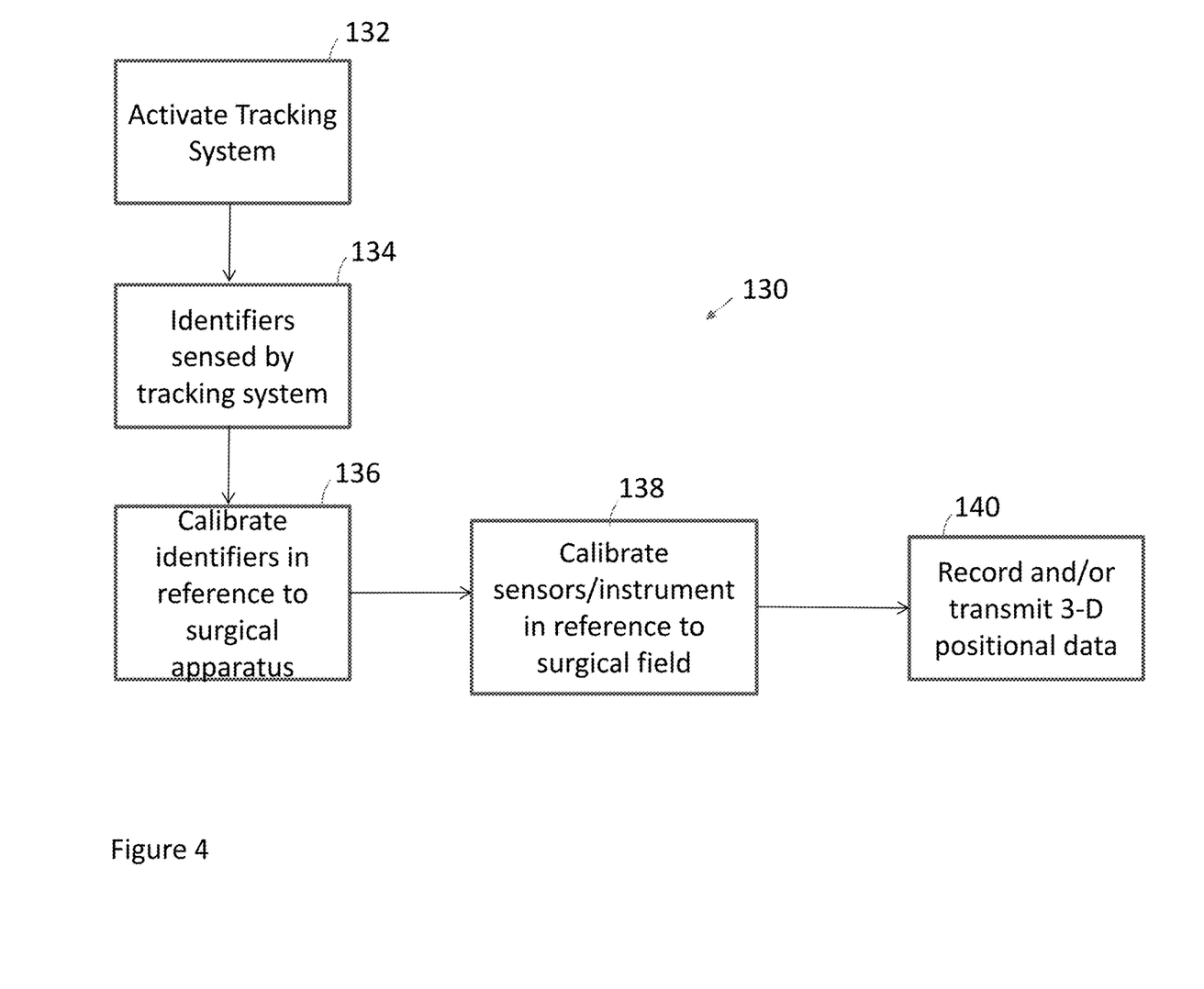
FIG. 4 is a flowchart of an exemplary embodiment of a method for tracking the surgical treatment apparatus relative to a patient's anatomical structure by the surgical navigation system in accordance with an embodiment of the present disclosure.

Referring now to FIG. 4, a flow chart 130 describing the operation of the tracking system 20 is shown. Initially, as represented by step 132, the tracking system 20 is activated, for example, through the use of the tracking system software 30. Then, the tracking system 20 locates the position and orientation of the bone plate 60 in a step 134 by analyzing sensor data, such as images depicting the identifiers 18 of the bone plate 60 or by the position of the bone plate to the identifiers 18 of the bone plate holder (not shown). Optionally, at a step 136, the tracking system 20 may calibrate the identifiers 18 in reference to the position and orientation of the surgical treatment apparatus 12, e.g., the bone plate 60. This may include placing the surgical treatment apparatus 12 in a known position and orientation, and/or rotating and orienting the surgical treatment apparatus 12 in various known positions. In step 138, the identifiers 18 may be calibrated in reference to the surgical field, for example, by placing the surgical treatment apparatus 12 in pre-determined locations within the surgical field. Finally, in step 140, the tracking system 20 can record and/or transmit the three-dimensional positional data obtained from the identifiers 18 to the computer system 24.

Figure 5:
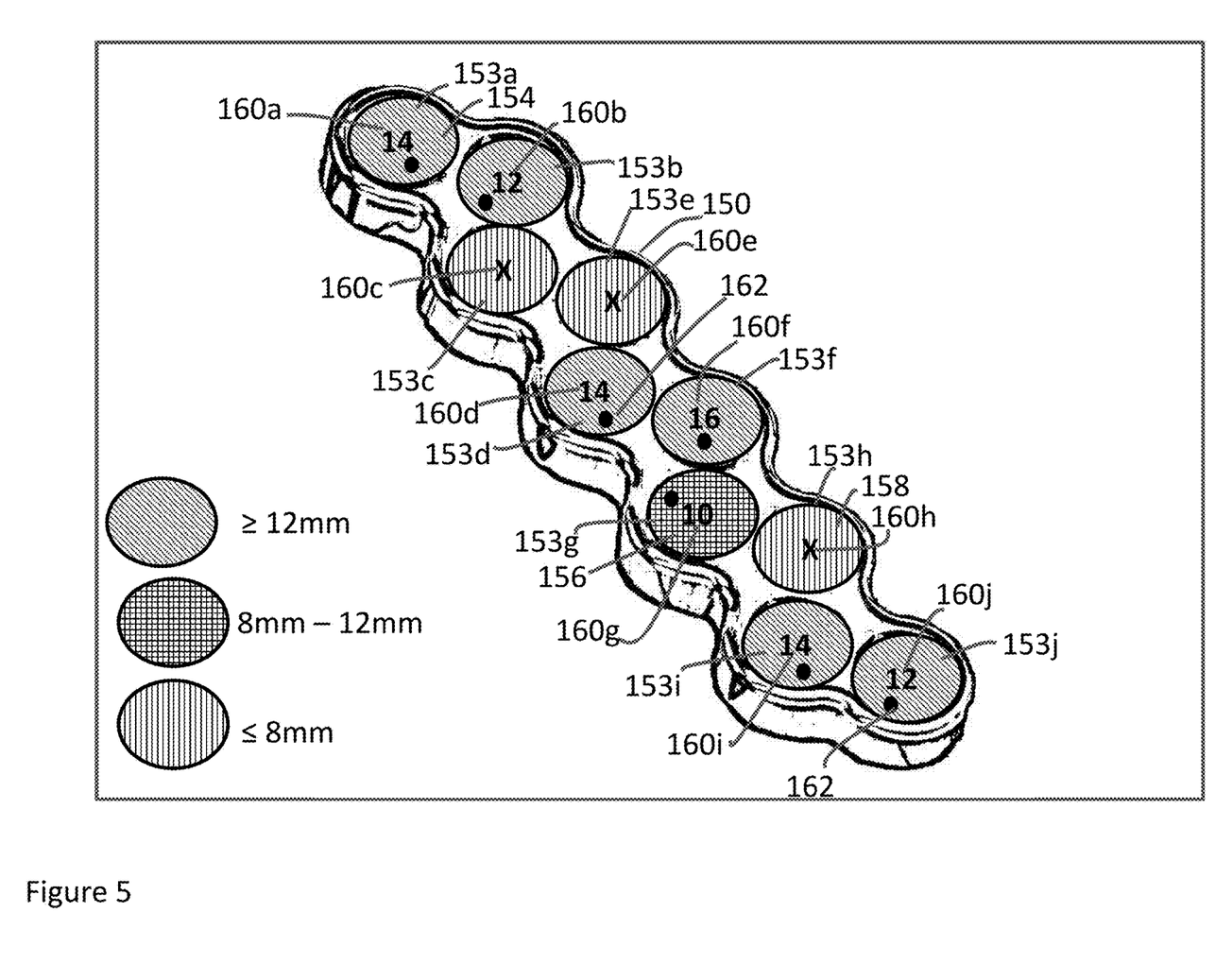
FIG. 5 is an exemplary illustration of a surgical treatment apparatus with superimposed surgical indications indicative of attachment metrics in accordance with the present disclosure.

Referring now to FIG. 5, shown therein is a graphical representation 150 of the surgical treatment apparatus 12 with superimposed indications indicative of one or more attachment metrics on a hole by hole basis. The graphical representation 150 of the surgical treatment apparatus 12 is derived from the 3D geometry database 40. The graphical representation 150 can be selected by selecting a particular surgical treatment apparatus 12 to use in a given surgical procedure. The three-dimensional geometric data of the surgical treatment apparatus 12, along with the positional data of the surgical treatment apparatus 12 allows the computer system 24 to calculate the position of the surgical treatment apparatus 12 in a three-dimensional space. The computer system 24 utilizing the image interpretation software 42 can calculate various attachment metrics for each hole 80 within the surgical treatment apparatus 12 and may denote the hole 80 with a corresponding color. For example, a fastener-in-bone integration metric 153a-j may have several levels, and may be indicated with the following: a first area 154 registered on a particular hole 80 for strong fastener-in-bone-integration, a second area 156 registered on particular hole 80 for a relatively weaker fastener-in-bone integration, and a third area 158 registered on a particular hole 80 for poor fastener-in-bone integration 35. More or less areas, and/or type of indications indicative of the level of fastener-in-bone integration can be used. The computer system 24 may also calculate an optimal length of the fastener necessary to achieve the indicated level of fastener-in-bone integration, and can denote a fastener length indication 160a-j on particular holes 80. For example, the fastener length indication 160 can be displayed as text in millimeters on each hole 80. When fastener length is below a certain amount that makes applying a fastener through the hole 80 undesirable, the fastener length indication 160 can be displayed with a symbol, such as "X." The computer system 24 may also determine optimal bone plate 60 placement by calculating the average fastener-in-bone integration strength among all holes at a given position, whereby the highest average fastener-in-bone integration position can indicate optimal bone plate 60 placement. The computer system 24 may also calculate a fastener trajectory to secure the surgical treatment apparatus 12 to the patient's anatomical structure 14 and denote an optimal trajectory. This can be accomplished, for example, by creating a registered coordination system by matching the patient's tomography or three-dimensional ultrasound image data with the patient's position during surgery through a registration process, such as point-set registration or surface matching routines, and then calculating trajectory as a vector defined by two points: the final position of the distal fastener tip and the position of the midline of the fastener hole crossing the surface plane of the bone plate 60. Optimal trajectory may be denoted by applying a graphical representation of a fastener trajectory indication 162 on the representation of the hole 80 that is offset from a central location of the hole 80 to indicate the trajectory. The surgical treatment apparatus 12 of FIG. 5 can be superimposed onto the three-dimensional reconstruction of the surgical field and then shown on the display device 26.

Figure 6:
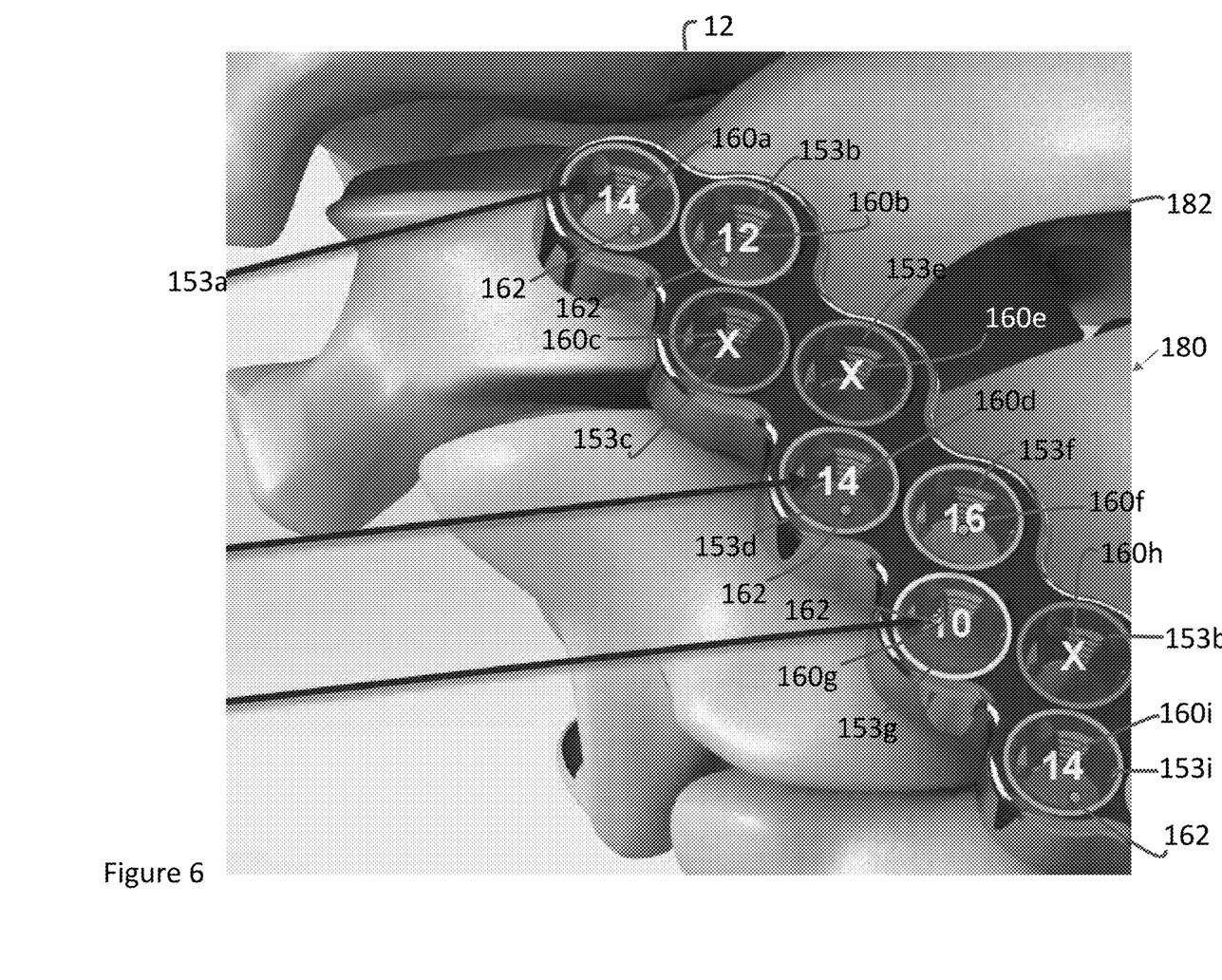
FIG. 6 exemplary screenshot of a display in accordance with an embodiment of the disclosure showing attachment metrics calculated by the system.

Referring now to FIG. 6, an exemplary display 180 provided by the display device 26 consistent with the preferred embodiment of the disclosure is shown. The display 180 includes a primary window that provides the surgeon with a three-dimensional reconstruction 182 of the surgical field including the patient's anatomical structure 14 and a superimposed representation 184 of the surgical treatment apparatus 12, including the indications 153, 160, and 162 indicative of the attachment metrics calculated by the computer system 24. The fastener-in-bone-integration indication 153 is shown, for example, as a color overlaying each hole 80. The fastener length indication 160 is shown as text on the fastener-in-bone-integration indication 153 and may be denoted, for example, in millimeters. The fastener trajectory indication 162 is shown, for example, by placing a small dot within each individual fastener hole 29. The attachment metrics for each hole 80 may change as the surgical treatment apparatus 12 is moved relative to the patient's anatomical structure 14. Further, other types of indications may be used to indicate fastener-in-bone integration, fastener length, and trajectory, and/or other useful metrics. Other control windows and displays may be available for the surgeon to vary system parameters and control other aspects of functionality.

Figure 7A:
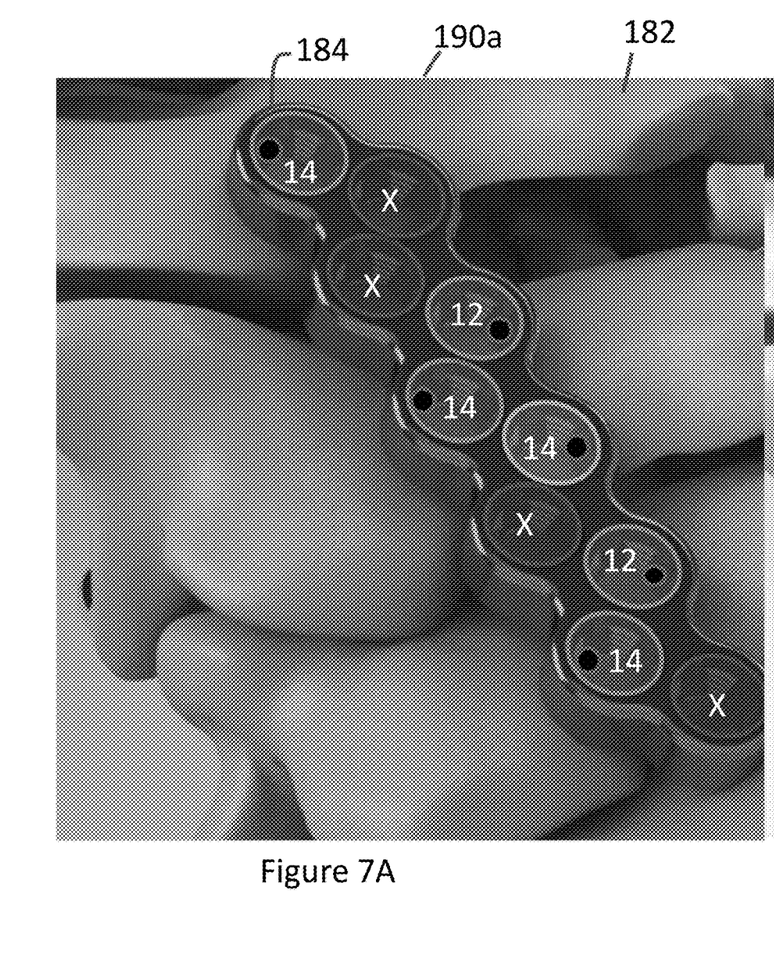
FIGS. 7A and 7B are exemplary screenshots of a display in accordance with an embodiment of the disclosure showing updated attachment metrics based on a change in position of the surgical treatment apparatus.
Figure 7B:
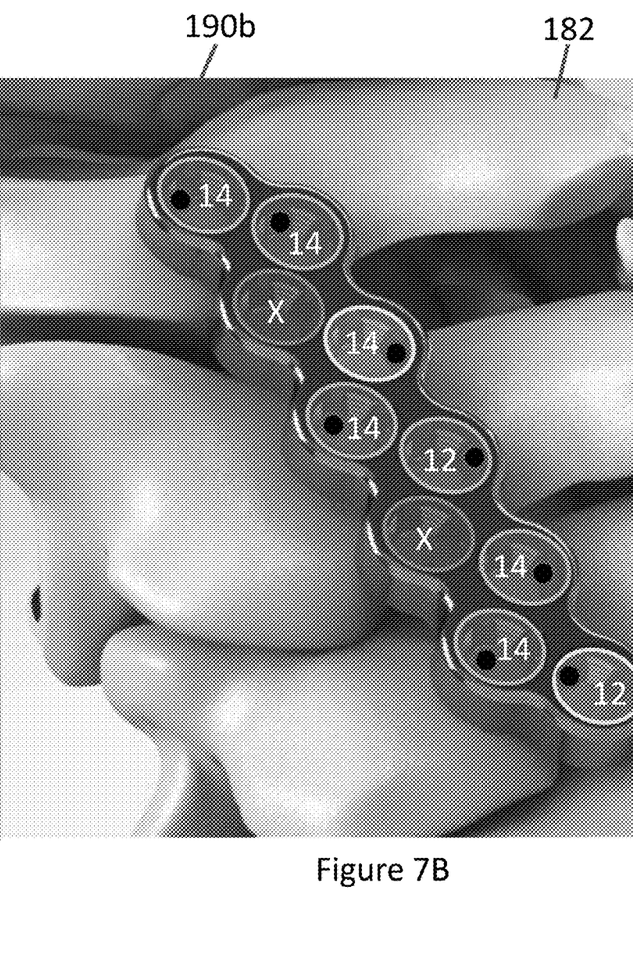

Referring now to FIGS. 7A and 7B, exemplary displays 190a and 190b consistent with the preferred embodiment of the disclosure is shown. FIG. 7A depicts the three-dimensional reconstruction 182 of the surgical field including the patient's anatomical structure 14 and the superimposed representation 184 of the surgical treatment apparatus 12, showing, for example, six holes 80 with strong fastener-in-bone integration and four holes 80 with weak fastener-in-bone integration. FIG. 7B depicts the same three-dimensional reconstruction 182 of the surgical field including the patient's anatomical structure 14 and the superimposed representation 184 of the surgical treatment apparatus 12 when the surgical treatment apparatus 12 has been moved, for example, 3 mm in a cranial direction. The movement of the surgical treatment apparatus 12 results in updated recalculation of the attachment metrics, in this example, eight individual holes 80 with strong fastener-in-bone integration and two holes 80 with weak fastener-in-bone integration. The real-time recalculation of attachment metrics, allows a surgeon to identify an optimal position for placing the surgical treatment apparatus 12 with regards to the patient's anatomical structure 14. For example, the surgeon may identify an optimal position of the surgical treatment apparatus 12 with reference to the fastener-in-bone integration metric by calculating the ratio of holes 80 indicated as having strong fastener-in-bone integration 35 and holes 80 indicated as having weak fastener-in-bone integration 35.

From the above description it is clear that the present disclosure is well adapted to carry out the objects and to attain the advantages mentioned herein as well as those inherent in the disclosure. While presently preferred embodiments of the disclosure have been described for the purposes of this disclosure, it will be understood that numerous changes may be made which will readily suggest themselves to those skilled in the art and which are accomplished within the spirt of the disclosure disclosed and as defined in the appended claims.

What is claimed is:

1. A surgical navigation system, comprising:
   a tracking system configured to track a three-dimensional position and orientation of a surgical treatment apparatus having an identifier, the surgical treatment apparatus being a surgical implant, the surgical treatment apparatus having a hole;
   a database containing data indicative of a three-dimensional geometry of the surgical treatment apparatus;
   a display device; and
   a computer system in communication with said tracking system and database, the computer system configured to execute instructions for:
      rendering a three-dimensional reconstruction of a patient's anatomical structure selected for surgery on the display device, the three-dimensional reconstruction based on a three-dimensional image of the patient's anatomical structure;
      acquiring the three-dimensional position of the surgical treatment apparatus from the tracking system;
      rendering, on the display device, a representation of the surgical treatment apparatus onto the three-dimensional reconstruction of the patient's anatomical structure; and
      calculating a first proposed attachment metric for a first fastener to pass through the hole and attach the surgical treatment apparatus and the patient's anatomical structure at a first position using the three-dimensional position of the surgical treatment apparatus relative to the patient's anatomical structure;
      calculating a second proposed attachment metric for a second fastener to pass through the hole and attach the surgical treatment apparatus and the patient's anatomical structure at a second position using the three-dimensional position of the surgical treatment apparatus relative to the patient's anatomical structure, wherein the first proposed attachment metric is a fastener pull-out performance metric and the second proposed attachment metric is a fastener pull-out performance metric; and
      rendering sequentially on the display device an indication of the first proposed attachment metric and the second proposed attachment metric.

2. The surgical navigation system of claim 1, wherein the fastener pull-out performance metric is indicative of a wedge angle formed between a patient's anatomical structure and the first and second fastener, and wherein calculating the fastener pull-out performance metric comprises analyzing a current position of the surgical treatment apparatus overlying the patient's anatomical structure to determine the wedge angle generated by the patient's anatomical structure and the first and second fastener, and wherein a largest wedge angle is then used to determine the fastener pull-out performance metric.

3. The surgical navigation system of claim 1, wherein the display device is located in a location other than where the patient is receiving surgical treatment.

4. A method, comprising:
   rendering, on a display device, a representation of a surgical treatment apparatus, the surgical treatment apparatus being a surgical implant, and the surgical treatment apparatus having a hole, onto a three-dimensional reconstruction of a patient's anatomical structure based upon a three-dimensional position and orientation of the surgical treatment apparatus relative to the patient's anatomical structure;
   calculating a first proposed attachment metric for a first fastener to pass through the hole and attach the surgical treatment apparatus and the patient's anatomical structure at a first position using the three-dimensional position and orientation of the surgical treatment apparatus relative to the patient's anatomical structure;
   calculating a second proposed attachment metric for a second fastener to pass through the hole and attach the surgical treatment apparatus and the patient's anatomical structure at a second position using the three-dimensional position of the surgical treatment apparatus relative to the patient's anatomical structure, wherein the first proposed attachment metric is a fastener pull-out performance metric and the second proposed attachment metric is a fastener pull-out performance metric; and
   rendering sequentially on the display device an indication of the first proposed attachment metric and the second proposed attachment metric, the indication superimposed over the representation of the surgical treatment apparatus.

5. The method of claim 4, wherein the representation of the surgical treatment apparatus is called from a database which includes dimensions of the surgical treatment apparatus.

6. A non-transitory computer readable medium comprising computer executable code that when executed by at least one computer processor causes the computer processor to:
   render, on a display device, a representation of a surgical treatment apparatus onto a three-dimensional reconstruction of a patient's anatomical structure based upon a three-dimensional position and orientation of the surgical treatment apparatus relative to the patient's anatomical structure, the surgical treatment apparatus being a surgical implant having a hole;
   calculate a first proposed attachment metric for a first fastener to pass through the hole and attach the surgical treatment apparatus and the patient's anatomical structure at a first position using the three-dimensional position and orientation of the surgical treatment apparatus relative to the patient's anatomical structure;
   calculate a second proposed attachment metric for a second fastener to pass through the hole and attach the surgical treatment apparatus and the patient's anatomical structure at a second position using the three-dimensional position and orientation of the surgical treatment apparatus relative to the patient's anatomical structure, wherein the first proposed attachment metric is a fastener pull-out performance metric and the second proposed attachment metric is a fastener pull-out performance metric; and render sequentially on the display device an indication of the first proposed attachment metric and the second proposed attachment metric.

7. The non-transitory computer readable medium of claim 6, wherein rendering, on the display device, the representation of the surgical treatment apparatus includes:

rendering the surgical treatment apparatus from first data contained within a first database indicative of dimensions of the surgical treatment apparatus;

rendering the patient's anatomical structure from second data contained within a second database indicative of at least one tomography image or ultrasound image of the patient's anatomical structure; and acquiring and analyzing sensor data indicative of the three-dimensional position and orientation of the surgical treatment apparatus relative to the patient's anatomical structure to determine the three-dimensional position and orientation of the surgical treatment apparatus relative to the patient's anatomical structure.

8. The non-transitory computer readable medium of claim 6, wherein rendering, on the display device, the representation of the surgical treatment apparatus includes superimposing the representation of the surgical treatment apparatus onto the representation of the patient's anatomical structure.

9. The non-transitory computer readable medium of claim 6, wherein the indication of the first proposed attachment metric and the second proposed attachment metric includes one or more graphical indicators varying in size, shape, and color.

10. The non-transitory computer readable medium of claim 6, wherein the surgical treatment apparatus includes multiple holes, and wherein calculating the first proposed attachment metric and the second proposed attachment metric for the first and second fasteners, respectively, include calculating at least one attachment metric for each of the multiple holes.

* * * * *